(12) United States Patent
Vargas, Jr. et al.

(10) Patent No.: US 10,400,202 B2
(45) Date of Patent: Sep. 3, 2019

(54) ENHANCED PHOTOBIOREACTOR SYSTEM

(71) Applicants: Jose Viriato Coelho Vargas, Jr., Curtiga Parana (BR); Wellington Balmant, Curitiba Parana (BR); Alexandre Stall, Curitiba Parana (BR); Andre Bellin Mariano, Curitiba Parana (BR); Juan Carlos Ordonez, Tallhassee, FL (US); Zohrob Hovsapian, Tallhassee, FL (US); Emerson Dilay, Curitiba (BR)

(72) Inventors: Jose Viriato Coelho Vargas, Jr., Curtiga Parana (BR); Wellington Balmant, Curitiba Parana (BR); Alexandre Stall, Curitiba Parana (BR); Andre Bellin Mariano, Curitiba Parana (BR); Juan Carlos Ordonez, Tallhassee, FL (US); Zohrob Hovsapian, Tallhassee, FL (US); Emerson Dilay, Curitiba (BR)

(73) Assignee: The Florida State University Research Foundation Incorporated, Tallahassee, FL (US)

(*) Notice: Subject to any disclaimer, the term of this patent is extended or adjusted under 35 U.S.C. 154(b) by 92 days.

(21) Appl. No.: 15/362,182

(22) Filed: Nov. 28, 2016

(65) Prior Publication Data
US 2017/0073622 A1  Mar. 16, 2017

Related U.S. Application Data

(63) Continuation-in-part of application No. 14/736,623, filed on Jun. 11, 2015, now abandoned, which is a (Continued)

(51) Int. Cl.
  *C12M 1/12* (2006.01)
  *C12N 1/12* (2006.01)
  *C12M 1/00* (2006.01)

(52) U.S. Cl.
  CPC ............ *C12M 21/02* (2013.01); *C12M 23/06* (2013.01); *C12M 29/04* (2013.01); *C12M 43/02* (2013.01); *C12N 1/12* (2013.01)

(58) Field of Classification Search
  CPC ...... C12M 21/02; C12M 23/06; C12M 23/22; C12M 29/04; C12M 31/02; C12M 31/08;
  (Continued)

(56) References Cited

U.S. PATENT DOCUMENTS

| | | | |
|---|---|---|---|
| 2008/0032396 A1* | 2/2008 | Chokshi ................. | C12M 23/08 435/294.1 |
| 2010/0159579 A1* | 6/2010 | Schuring ................ | C12M 21/02 435/292.1 |
| 2012/0021498 A1* | 1/2012 | Muller-Feuga ........ | C12M 21/02 435/257.1 |

* cited by examiner

*Primary Examiner* — Michael L Hobbs
(74) *Attorney, Agent, or Firm* — J. Wiley Horton

(57) ABSTRACT

A space efficient photo-bioreactor. The bioreactor grows microalgae in a tall array of transparent flooded tubes. A nutrient media is circulated through the tubes. The array is configured to maximize the amount of sunlight falling upon each tube so that growth of the microalgae is as uniform as possible. A vertically-oriented gasser tube is provided. Gas is injected into this gasser tube along with the liquid nutrient medium. A bubble-size limiter is employed in the gas injector. The flow rates are configured so that the liquid nutrient medium and injected gas remain within the vertical gasser tube for 30 seconds or more.

7 Claims, 9 Drawing Sheets

Related U.S. Application Data continuation-in-part of application No. 13/271,622, filed on Oct. 12, 2011, now abandoned.

(60) Provisional application No. 61/392,053, filed on Oct. 12, 2010.

(58) Field of Classification Search
CPC ...... C12M 31/12; C12M 31/00; C12M 43/02; C12M 43/06; C12N 13/00; C12P 5/023; C12P 7/649; C05F 3/32; A01G 33/00; Y02E 50/13; Y02E 50/343
USPC ...................................................... 435/292.1
See application file for complete search history.

ENHANCED PHOTOBIOREACTOR SYSTEM

CROSS-REFERENCES TO RELATED APPLICATIONS

This application is a continuation-in-part of prior U.S. application Ser. No. 14/736,623, which itself claims the benefit of prior application Ser. No. 13/271,622, provisional application Ser. No. 61/392,053.

STATEMENT REGARDING FEDERALLY SPONSORED RESEARCH OR DEVELOPMENT

None.

MICROFICHE APPENDIX

Not Applicable

BACKGROUND OF THE INVENTION

1. Field of the Invention

This invention relates to the field of renewable energy. More specifically, the invention comprises a space-efficient photo-bioreactor and methods for controlling the bioreactor.

2. Description of the Related Art

The continued use of petroleum-derived fuels is now widely seen as unsustainable.

However, much of the existing transportation structure is dependent upon the combustion of liquid fuels. Changing to a completely different energy source—such as battery power—is at present unrealistically expensive and inefficient.

On the other hand, presently available biofuels can be substituted for petroleum-derived fuels without the need for extensively modifying existing internal combustion engines. One promising alternative fuel is biodiesel, which can be substituted for petroleum diesel in many modern engines (albeit with a slight reduction in specific energy).

Oil crops can be used to make biodiesel. These are attractive, as the total cycle of production through consumption can be made carbon-neutral. Unfortunately, though, oil crops are not very space-efficient. It is estimated that if 24% of the total cropland in the United States was devoted to a high-yielding oil crop such as palm oil, this would still only meet about half of the demand for transportation fuels.

Microalgae-based bio-fuels hold the promise of much greater space efficiency. Like plants, microalgae use sunlight to produce oils. They do it much more efficiently than crop plants, though. Microalgae-based biodiesel is still in a developmental state in terms of cost efficiency. However, it is clear that biodiesel can be made from microalgae. In order to make such a process economically efficient, it is important to use as many of the products produced as possible.

It is known to cultivate algae in a series of ponds. While this method does work, it is not space efficient. In fact, using the open-pond method, more surface area is needed to grow a given mass of biofuel than would be needed for conventional row crops yielding the same amount of biofuel. In order to realize the potential of microalgae-based fuels, then, it is far preferable to provide a more space-efficient system.

Further, prior art photo-bioreactors typically require concentrated carbon dioxide as a feed material for the photosynthesis. Concentrated carbon dioxide must be collected, transported, and stored. Even if an on-site source is available, it must still be segregated from the surrounding air. It would be preferable to provide a photo-bioreactor that can run on ordinary air. Such a reactor would still be useful in removing carbon dioxide from the atmosphere, but would eliminate the need to separately collect and store the carbon dioxide.

The present invention is able to run on ordinary air. The present invention is also quite space efficient. These and other advantages will be explained in the following descriptions.

BRIEF SUMMARY OF THE INVENTION

The present invention comprises a space efficient photo-bioreactor system. The bioreactor grows microalgae in a tall array of transparent flooded tubes. A nutrient media is circulated through the tubes. The array is configured to maximize the amount of sunlight falling upon each tube so that growth of the microalgae is as uniform as possible.

In the preferred embodiments a vertical support structure is provided for the array of tubes. A reservoir is located on the top of this structure. Flow from the reservoir branches into multiple, independent flow paths. Each independent flow path includes a serpentine array of transparent tubes. A liquid pump or pumps collects the flow from the flow paths, pressurizes it, and pumps it back to the reservoir. A vertically-oriented gassing tube carries the flow from the pump back up to the reservoir. Air, or other $CO_2$-containing gas, is injected near the bottom of the gassing tube. The size of the gas bubbles is controlled by injecting through appropriate metering openings. The gas diffuses through the liquid medium as the mixture rises in the gasser tube.

Microalgae are harvested from the photo-bioreactor and processed for various suitable uses. One use is the manufacturing of biodiesel. The microalgae is filtered and dried. Lipids are then extracted from the microalgae. These lipids are made into biodiesel through a trans-esterification process. The lipids may be used to make other products as well.

Some of the biodiesel can be used to run a diesel engine to furnish electrical and/or mechanical power to the bioreactor. Exhaust gas emitted by the diesel engine is preferably fed back into the bioreactor. Carbon dioxide from other greenhouse gas sources is preferably also fed into the bioreactor.

REFERENCE NUMERALS IN THE DRAWINGS

| 10 | energy harvesting system | 12 | water tank |
|----|--------------------------|----|-----------|
| 14 | nutrients | 16 | nutrient tank |
| 18 | photo-bioreactor | 20 | harvesting unit |
| 22 | filtering unit | 24 | drying unit |
| 26 | lipids extraction unit | 28 | trans-esterification unit |
| 30 | biodiesel | 32 | diesel engine |
| 34 | carbon dioxide input | 36 | inoculum input |
| 38 | support frame | 40 | rack |
| 42 | bioreactor tube | 43 | sunlight |
| 44 | elbow | 46 | gassing/degassing system |
| 48 | housing | 50 | carbon dioxide inlet |
| 52 | oxygen outlet | 54 | aluminum helix |
| 56 | coolant inlet | 58 | coolant outlet |
| 60 | inlet | 62 | outlet |
| 64 | inlet manifold | 66 | outlet manifold |
| 68 | reservoir | 70 | liquid pump |
| 72 | gasser tube | 74 | gas injector |
| 76 | gas injector pump | 78 | gas inlet |
| 80 | tube column | 82 | tube column |
| 84 | tube row | 86 | mesh |
| 88 | pump intake line | 90 | pump discharge line |
| 92 | reservoir outlet line | | |

DETAILED DESCRIPTION OF THE INVENTION

Figure 1:
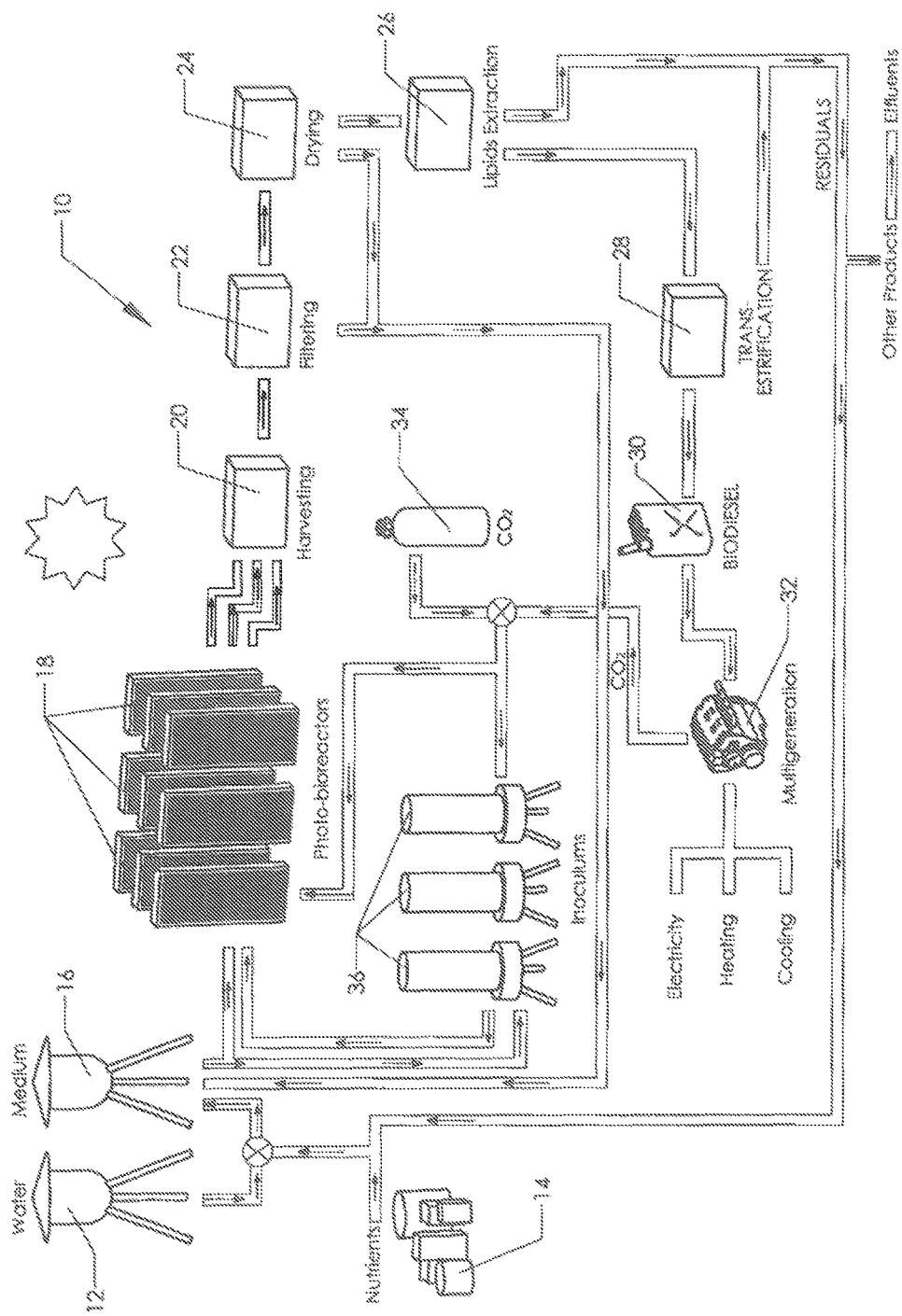
FIG. 1 is a schematic view, showing the operation of the photo-bioreactor and other related processes.

FIG. 1 shows a schematic view of a comprehensive energy harvesting system 10 based on one or more photo-bioreactors 18. The photo-bioreactors are preferably made as vertical structures having a relatively small "footprint" compared to the volume of liquid media they contain.

Nutrients 14 are mixed with water from water tank 12 (or other suitable water source) to create a nutrient medium which is preferably stored in nutrient tank 16. Inoculum input 36 is fed into a portion of the nutrient medium and this mixture is then fed into the photo-bioreactors.

Sunlight falling on the photo-bioreactors causes microalgae to grow inside. This is eventually harvested in harvesting unit 20. The product of the harvesting unit is then fed through filtering unit 22, where the microalgae is removed and residual nutrient medium is sent back to the photo-bioreactors.

The microalgae is then fed from filtering unit 22 to drying unit 24, where it is dried. The dried microalgae is then fed through lipids extraction unit 26. The extracted lipids are then sent to trans-esterification unit 28, which converts the lipids to biodiesel 30 using processes well known to those skilled in the art. The "waste" products from the lipids extraction unit are preferably fed back to the bioreactors.

The biodiesel thus produced can be transported and used as a substitute for conventional fuels. A portion of the biodiesel produced can also be used to run an on-site diesel generator. The generator can then provide power for the energy harvesting system 10.

The system preferably re-uses the products of each stage in the process. For example, the carbon dioxide produced by the on-site generator is preferably fed back into the bioreactors. More carbon dioxide will likely be needed for this embodiment—and this is furnished via carbon dioxide input 34.

Figure 2:
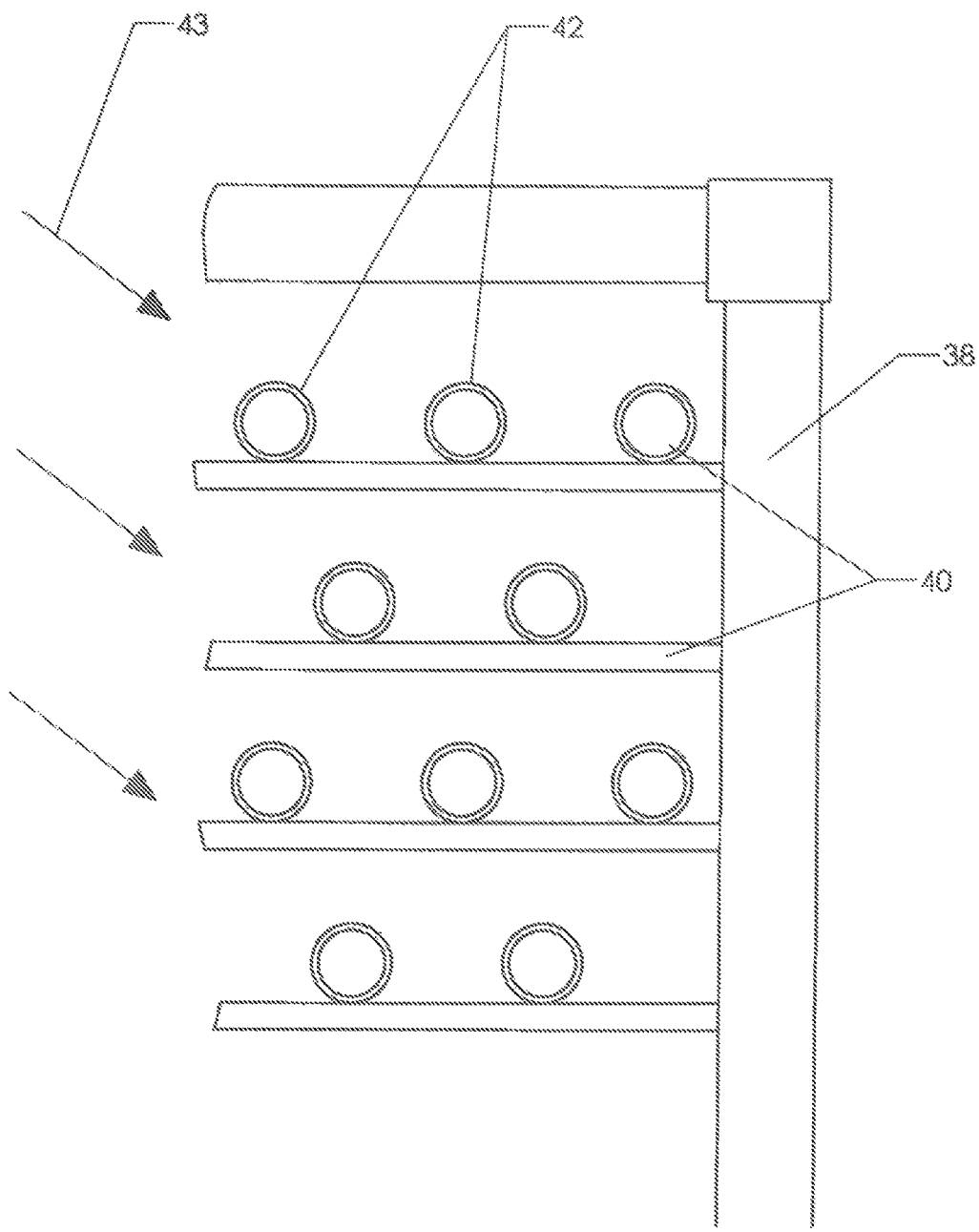
FIG. 2 is an elevation view showing the arrangement of the bioreactor tubes.

FIG. 2 shows a partial sectional elevation view through one of the photo-bioreactors. As mentioned previously, each photo-bioreactor preferably has a small footprint in comparison to the volume it contains. Support frame 38 supports a number of layered racks 40. Each rack 40 supports a number of bioreactor tubes 42. The tubes are relatively thin-walled transparent structures oriented perpendicularly to the view in FIG. 2. They are spaced (both horizontally and vertically) so that sunlight 43 can pass into the bioreactor and fall on each of the tubes.

Figure 3:
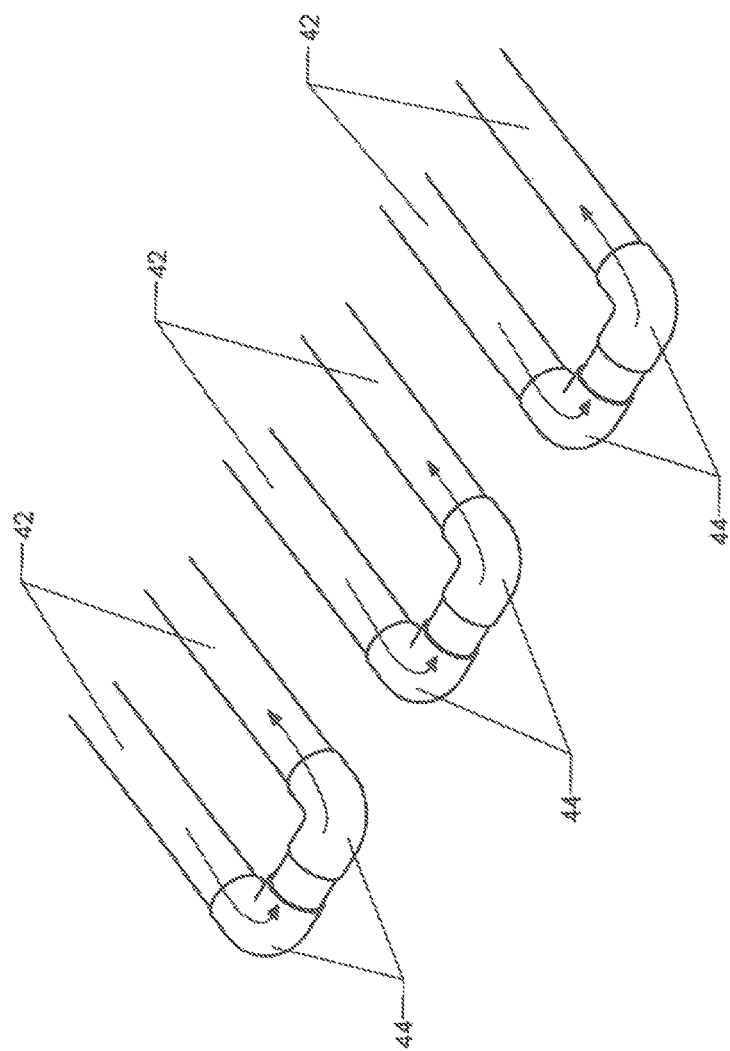
FIG. 3 is a perspective view, showing a typical circulation path for the bioreactor tubes.

The liquid nutrient medium flows through the tubes. The tubes are joined together so that an elongated flow path is created. FIG. 3 shows one approach to joining the tubes in one rack 40. Each tube has an inlet end and an outlet end. The terms "inlet end" and "outlet end" are arbitrary terms depending on the flow direction through a particular tube. Two adjacent tubes may be joined by installing an elbow 44 between the outlet end of one tube and the inlet end of the adjacent tube. Using several such elbows a serpentine flow path can be created as in FIG. 3 (Elbows are also provided at the opposite ends of the tubes. These are not shown). Vertically oriented elbows may also be provided to join tubes on different racks 40.

It is therefore possible to create a single serpentine flow path through the entire set of tubes in a bioreactor. Of course, it may also be desirable to create two, three, or many more individual flow paths in a single bioreactor. Many different flow paths may be created, depending upon how the tubes are connected. It is also possible to use valves to create changeable flow paths. A pump is generally used to circulate the nutrient medium.

Figure 4:
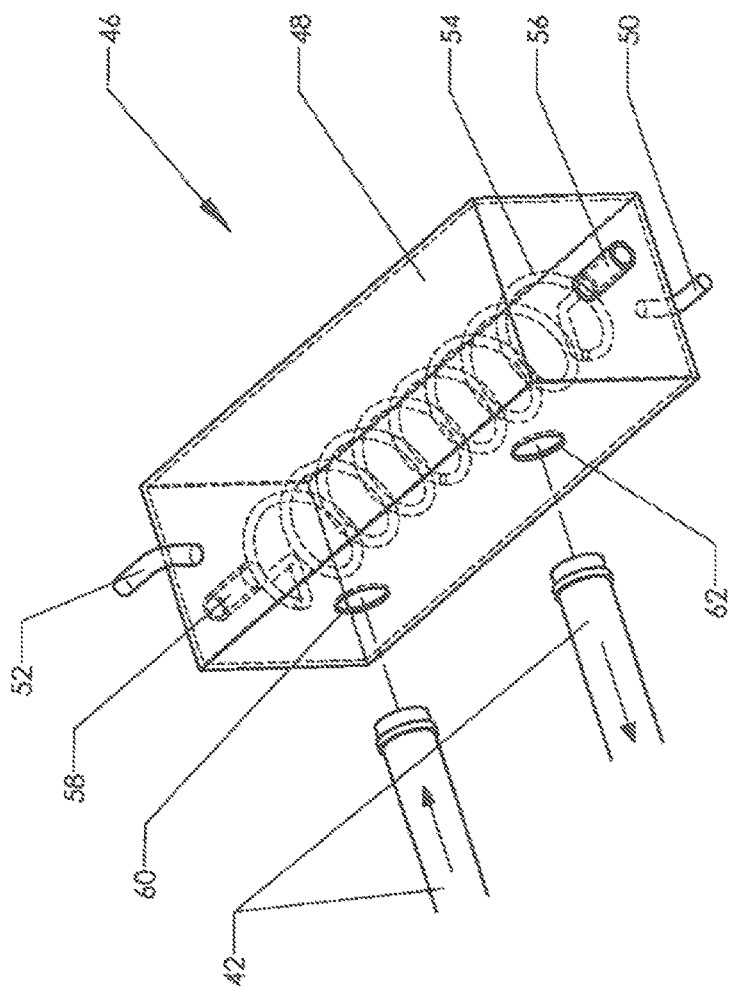
FIG. 4 is an exploded perspective view, showing a typical gassing/degassing system.

Since the microalgae growth depends on photosynthesis, carbon dioxide must be added to the circulating medium. It may also be desirable to remove the oxygen produced by the photosynthesis. FIG. 4 shows a simplified depiction of a device which can provide both of these functions. Gassing/degassing system 46 has housing 48. Two bioreactor tubes 42 are connected to housing 48. Inlet flow is provided through inlet 60. Outlet flow is provided through outlet 62. Thus, the interior of housing 48 is part of a flow path within the bioreactor.

Carbon dioxide inlet 50 introduces carbon dioxide. Oxygen outlet 52 allows the escape and collection of oxygen. It may also be desirable to maintain the circulating medium at a particular temperature. Thus, a heat exchange device is also provided. Aluminum helix 54 is a hollow tube. Coolant inlet 56 provides inlet cooling flow through the aluminum helix. Coolant outlet carries away the coolant flow. The coolant used can be water which is cooled by a separate chiller. Other coolants may of course be used as well.

Several gassing/degassing systems 46 can be installed at suitable locations within the flow path of the bioreactor. Returning to FIG. 3, the reader will recall that simple elbows 44 may be used to direct the flow from one bioreactor tube 42 to another. Turning now to FIG. 4, those skilled in the art will realize that a gassing/degassing system 46 can be substituted for any of the elbows (with suitable adjustment being made for the distance between inlet 60 and outlet 62).

The bioreactor is largely a collection of simple components—such as a vertical rack with multiple horizontal tubes in an appropriately spaced location. The connections between many of the tubes will be made with elbows 44. The connection between other adjacent tubes will be made using a gassing/degassing system 46. The "control and monitoring" component is preferably part of gassing/degassing system 46. It is preferable to incorporate numerous components in housing 48. For example, the housing can contain and/or mount:
   (1) carbon dioxide injecting systems;
   (2) oxygen removal systems;

(3) carbon dioxide sensors;
(4) oxygen sensors;
(5) pH sensors;
(6) turbidity sensors;
(7) flow sensors; and
(8) temperature sensors.

As explained previously, the housing may also contain a heat exchanger capable of maintaining a desired temperature for the circulating medium. This would typically be a liquid-to-liquid heat exchanger. However—in some ambient environments—it may be possible to use a liquid-to-air exchanger. The systems for adding carbon dioxide and removing oxygen are well known in the art and will thus not be described in detail. The same may be said of the various sensors disclosed.

Figure 5A:
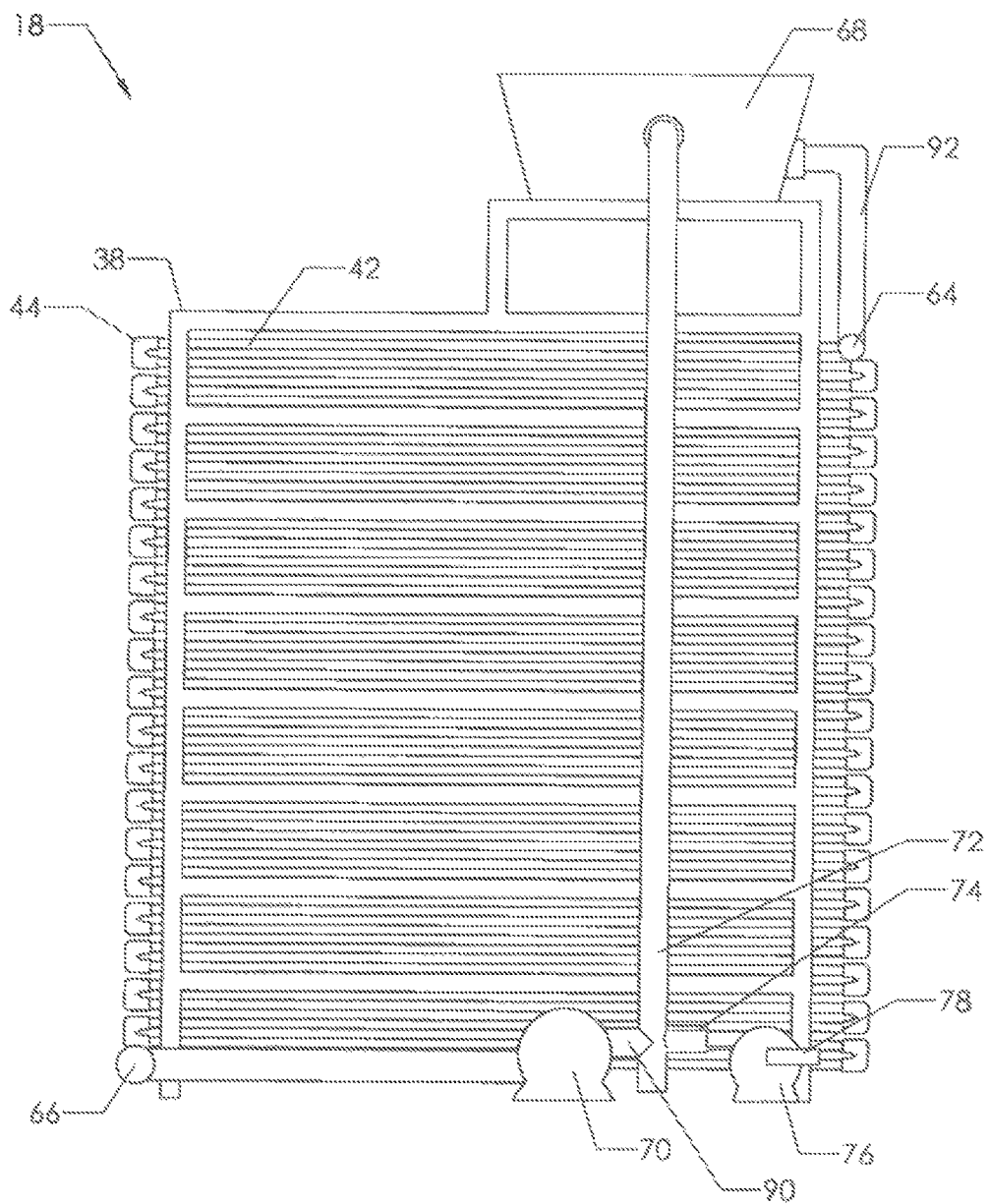
FIG. 5A is a side elevation view, showing an exemplary photo-bioreactor.

Space efficiency is a significant goal for the inventive photo-bioreactor. FIGS. 5A-6B show a preferred embodiment that minimizes the amount of ground surface area required. FIG. 5A shows how the components of photo-bioreactor 18 are generally supported by frame 38. The nutrient medium is collected in reservoir 68 near the top of the assembly. The circulating medium flows out from the reservoir through reservoir outlet line 92 into inlet manifold 64. The inlet manifold feeds the liquid into multiple, independent flow paths.

In the embodiment shown, each independent flow path comprises a serpentine path of bioreactor tubes 42 connected by elbows 44. Each serpentine flow path creates one vertical "column" within the assembly. In this example there are fourteen such columns. Each column is fed circulating liquid by inlet manifold 64. Outlet manifold 66 collects the liquid as it exits each column. From the outlet manifold the liquid is fed to liquid pump 70. The liquid pump pressurizes the collected liquid medium and feeds it up through gasser tube 72 and back to reservoir 68.

Gas injector pump 76 takes in a desired gas through gas inlet 78. It pressurizes this gas beyond the pressure within the lower portion of gasser tube 72 and injects the gas into the liquid medium through gas injector 74. In the preferred embodiments the injected gas is simply ambient air. Thus, gas inlet 78 is configured to suck in ambient air—possibly using an appropriate filter to exclude dust and other particles.

The mixture of liquid medium and injected gas travels upward together within gasser tube 72. The gas and liquid remain in contact throughout this period. At the top of the gasser tube the contents empty into reservoir 68 and the circulation loop begins again.

Figure 5B:
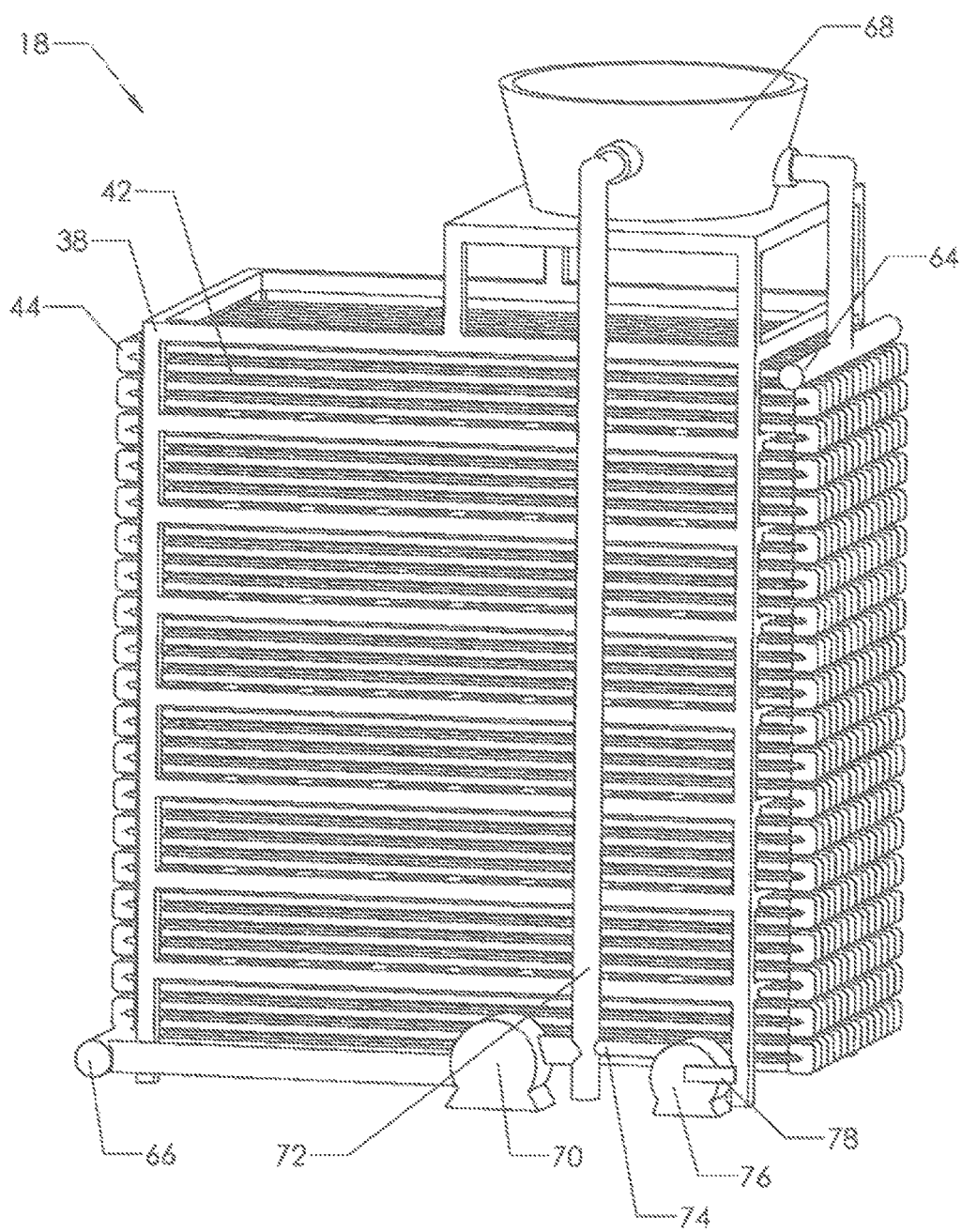
FIG. 5B is a perspective view, showing the photo-bioreactor of FIG. 5A.

FIG. 5B shows a perspective view of the same assembly. The reader should bear in mind that the depictions of the components are somewhat simplified. For example, the liquid and gas pumps are represented in a symbolic form. In addition, the bioreactor tubes and elbows are not necessarily drawn to the exact scale of a working unit.

Figure 6A:
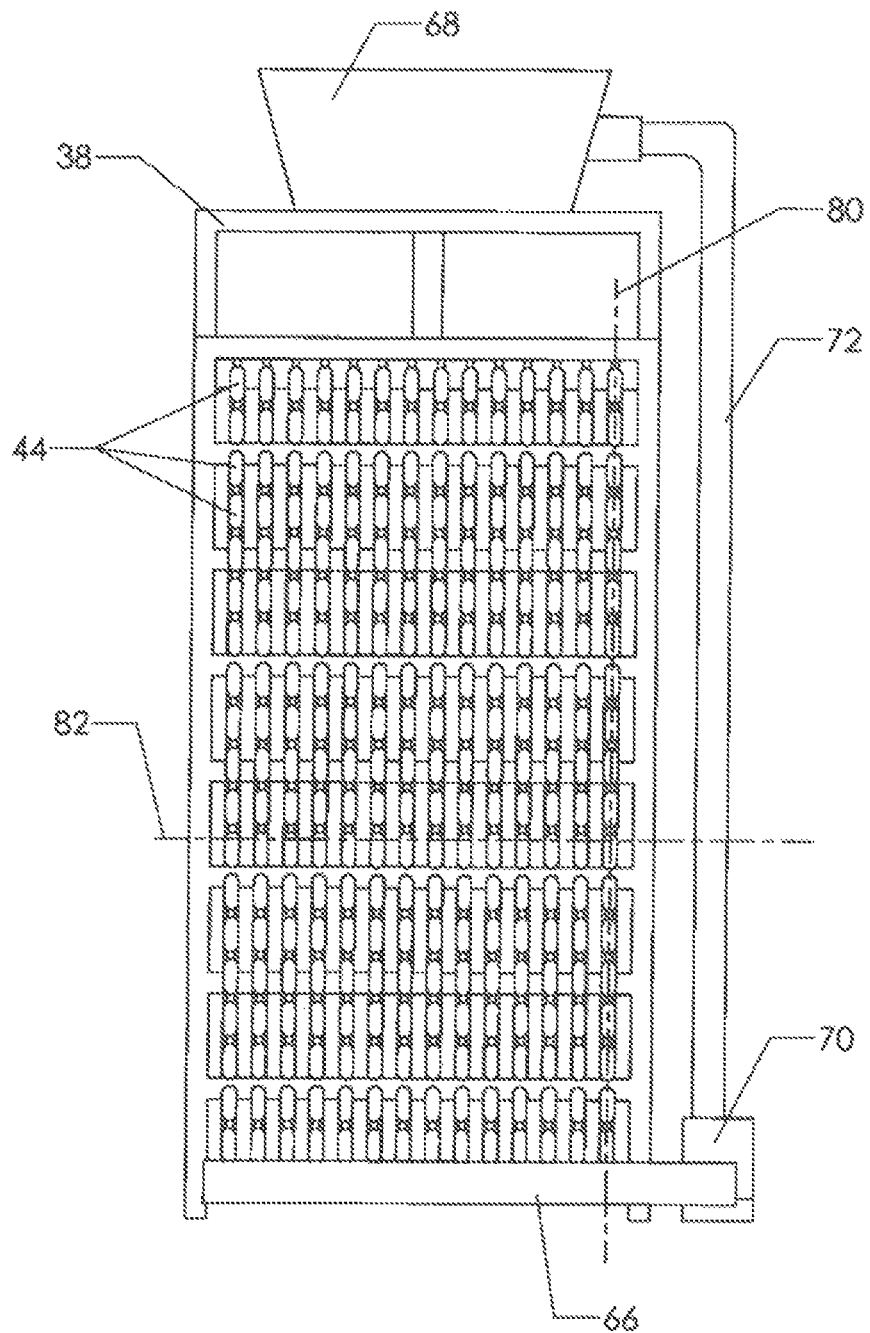
FIG. 6A is a front elevation view, showing the photo-bioreactor of FIG. 5A.

FIG. 6A shows a front elevation view of the same assembly. In this view the user may easily perceive how the array of bioreactor tubes is arranged into vertical columns and horizontal rows. In this embodiment there are fourteen vertical columns 80 of bioreactor tubes. There are thirty-nine horizontal rows 82 of tubes in each vertical column (Other embodiments may include fifty or more rows in each vertical column). Each column represents an independent flow path. Each column is fed liquid medium through inlet manifold 64. The liquid medium then flows through the column's serpentine path until it reaches outlet manifold 66. In outlet manifold 66 the independent flow paths are reunited.

Figure 6B:
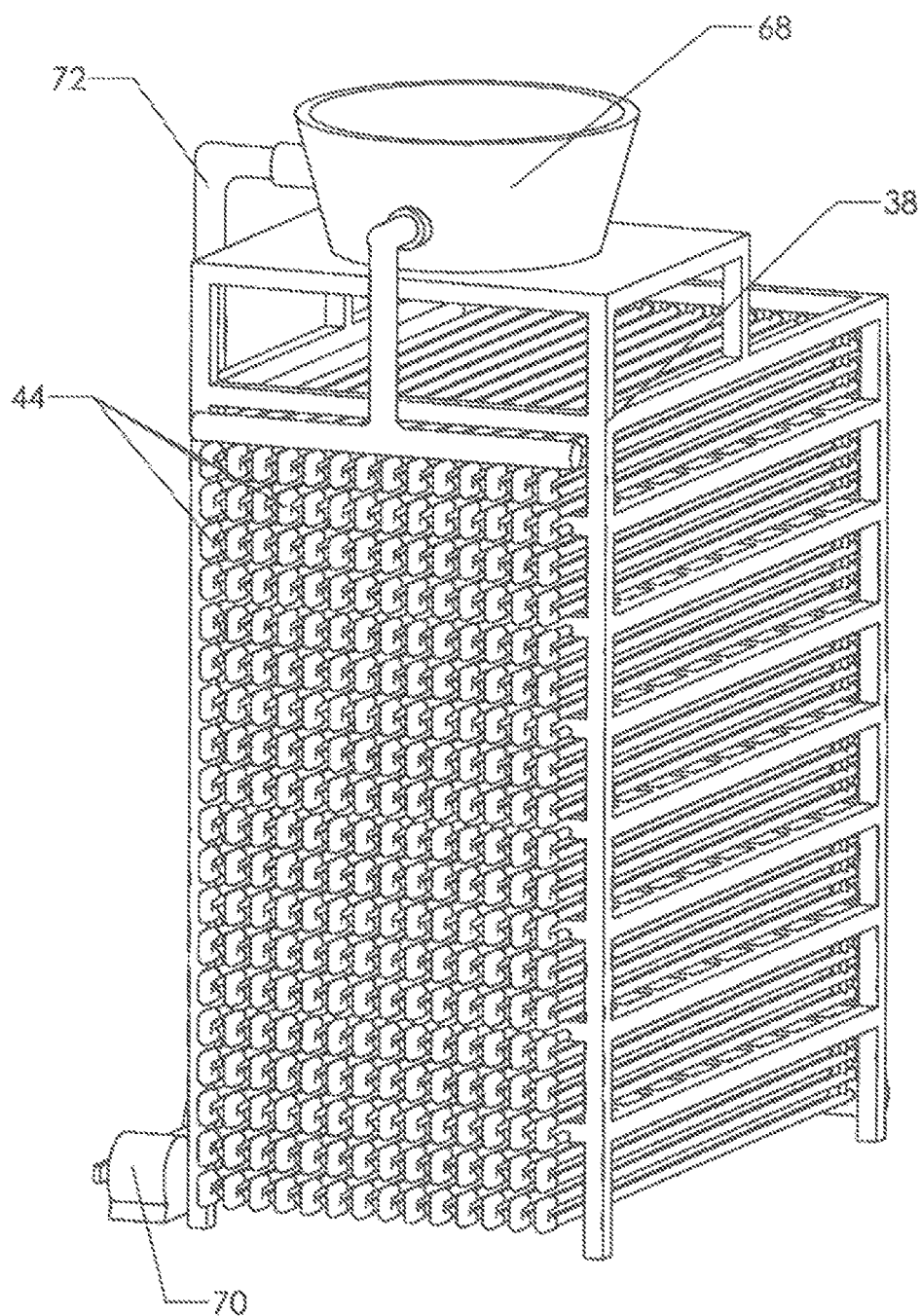
FIG. 6B is a front perspective view, showing the photo-bioreactor of FIG. 5A.

Pump intake line 88 takes the liquid from the outlet manifold to liquid pump 70. Of course, each column could have its own, separate return line to the liquid pump. The use of inlet manifold 64 and outlet manifold 66 represents only one way among many to create the desired flow paths. In addition, the inlet and outlet manifolds would typically include valves allowing each column to be taken out of the circulation loop for harvesting of the biomass, cleaning, or some other purpose. These valves have not been shown for purposes of visual clarity. FIG. 6B provides a perspective view of the opposite end of the assembly (opposite to the end shown in FIG. 6A).

Returning to FIG. 5A, some additional features of the invention will be explained before turning to a discussion of dimensions for some of the preferred embodiments. A significant feature of the invention is its ability to promote the dissolving of gas into the circulating liquid by enhancing the gas/liquid interface. The injected gas is preferably air from the surrounding atmosphere. The percentage of carbon dioxide in this air will typically be around 0.04% by volume. The photo-bioreactor relies in part on carbon dioxide and it is therefore important to dissolve the available carbon dioxide into the water as efficiently as possible.

In prior art systems gaseous, concentrated carbon dioxide is injected into a liquid volume and allowed to "bubble through." The gas bubbles naturally rise and a free gas volume tends to accumulate at the top of any containment vessel used. This fact means that a significant volume of gas is surrounded only by other gas and has no opportunity to contact the liquid. The present invention reduces this problem and increases the rate at which the gas dissolves into the liquid.

Figure 7:
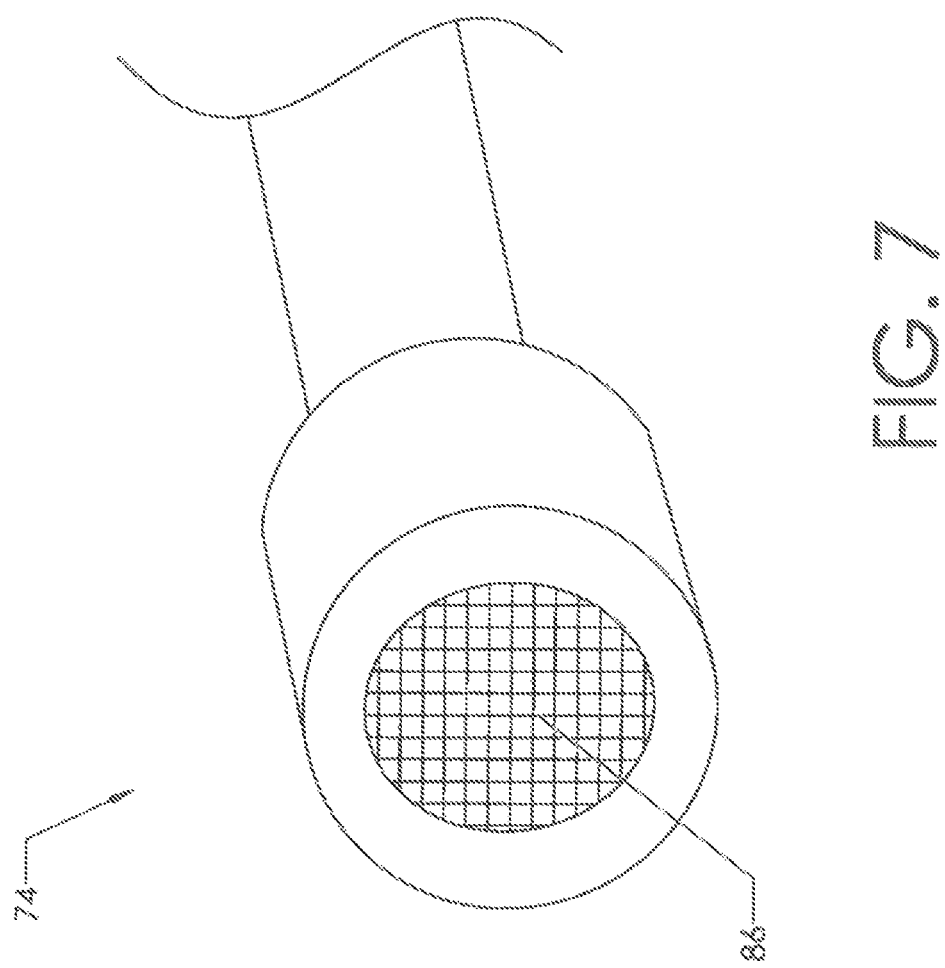
FIG. 7 is a detailed perspective view, showing a mesh that can be used in the air injector to limit bubble size.

Looking again at FIG. 5A, those skilled in the art will realize that the maximum pressure within the circulating system occurs at pump discharge line 90. The gas is injected very near this point of maximum pressure (Note location of gas injector 74). Further, the bubble size of the injected gas is controlled by using a suitable mesh or array of orifices. FIG. 7 shows the use of an exemplary mesh 86 across the injection opening. With appropriate injection pressure, this mesh produces small bubbles in the range of 0.5 mm to 1.0 mm. A smaller bubble creates a larger ratio of bubble surface area to bubble volume. This larger ratio enhances the solution rate.

Returning now to FIG. 5A, the reader will also observe how the gas bubbles are introduced at the bottom of a tall vertical column (gasser tube 72). This column may have a height of 15 meters or more. The gas bubbles flow upward with the ascending liquid. This maximizes the contact time between the gas and the liquid and prevents the formation of a large gas volume (though some aggregation of the bubbles will occur). Those skilled in the art will know that the bubble ascent rate is a strong function of bubble size, and that smaller bubbles ascend more slowly. The use of an injector that limits bubble size therefore increases the amount of time that the gas bubbles remain in gasser tube 72 (in addition to improving the surface area to volume ratio for each bubble).

The linear flow rate of the mixture within the gasser tube is a function of the volumetric flow of liquid pump 70 and the cross-sectional area of the gasser tube. A larger gasser tube produces a slower linear flow rate. Once the contents of the gasser tube reach the top they flow into reservoir 68. At this point any gas remaining will tend to migrate to the surface. Thus, it is preferable to design the components so that substantially all the injected gas is dissolved before the mixture reaches the reservoir. This may be done by matching the linear liquid flow rate in the gasser tube fairly closely to the bubble ascent rate, although some difference in the two velocities is desirable to promote turbulent flow.

Of course, in order to maximize the dissolution of the gas in the liquid, an excess amount of gas is preferable. Excess gas presents no problem for the preferred embodiments of the invention since they are injecting atmospheric air. Any excess gas may be vented back to the surrounding atmosphere.

The reader's understanding may benefit from some detailed explanation of the dimensions used in some of the preferred embodiments. In creating such a system, one may consider the following things, among others:

1. The diameter of the bioreactor tubes:
2. The overall length of each flow path;
3. The spacing of the bioreactor tubes (in order to ensure adequate sunlight exposure);
4. The flow rate within each flow path;
5. The dimensions of the gasser tube;
6. The flow rate within the gasser tube;
7. The injection of the gas; and
8. The overall "footprint" of the complete assembly.

A pilot scale photo-bioreactor has been developed and its dimensions are provided. The reader should bear in mind that both smaller and larger embodiments are possible. The pilot scale embodiment uses 3710 total meters of transparent PVC tubes. The tubes are given UV radiation protection. As shown in FIGS. 5A-6B, the tubes are arranged into vertical columns and horizontal rows. The tubes in each column are joined together by the elbows to create a serpentine flow path lying in a vertical plane. In a preferred embodiment, each independent flow path is 265 meters long. The external support frame 38 includes numerous cross pieces that support the tubes along their length (Most of these are not shown for purposes of visual clarity).

A preferred embodiment includes 14 vertical columns with 53 tubes in each column. Each of these tubes has an internal diameter of 5 cm. The straight vertical portion of gasser tube 72 is 8-16 meters long. It has an internal diameter of 10 cm. Each of the transparent tubes has a cross-sectional area of 19.6 square centimeters. Since there are 14 separate flow paths in this exemplary photo-bioreactor the combined cross-sectional area for all the tubes is 275 square centimeters. The cross-sectional area in the gasser tube is 78.5 square centimeters. Thus, the flow in each transparent tube is considerably slower than the flow in the gasser tube.

The entire assembly of FIGS. 5-6 occupies a compact volume. It is approximately 5 m long by 2 m wide by 10 m high. Despite its compact size, the inventive photo-bioreactor is capable of cultivating approximately 10,000 L of microalgae medium while using only 10 square meters of total surface area.

The components are depicted in somewhat-simplified form. The pump, for example, is not shown in detail. This component is preferably a diaphragm unit rather than a centrifugal one, as centrifugal pumps tends to harm the growing microalgae. In addition, numerous conventional components have not been depicted. For instance, it is desirable to include drain valves that allows the medium to be removed from the photo-bioreactor for filtering, drying, and further processing. Such valves may be located in the vicinity of outlet manifold 66, but they have not been illustrated. As explained in the following, it may also be necessary to include gas collection and removal chambers.

The inventive assembly maximizes the contact area and contact duration between the injected gas and the liquid medium. This feature increases the solution rate of the gas into the liquid medium and represents a significant advantage. A comparison of the inventive system to the prior art will serve to illustrate this advantage.

The prior art approach is to inject carbon dioxide into horizontal, tubular manifolds or large liquid holding tanks. In the case of a horizontal manifold, the injected gas tends to aggregate quickly into a layer at the top of the manifold. In the case of a holding tank the gas tends to bubble quickly through the liquid and then aggregate at the top or escape altogether.

A typical holding tank is about 1.5 meters deep. See, for example, the tanks 121-129 at FIG. 12 of U.S. Publication No. 2010/0159579. If gas bubbles are injected conventionally they tend to create an initial bubble size of about 0.75 cm or more. The bubble ascent rate for the smaller bubbles in this range is approximated by the expression:

$$v = \frac{1}{9}\left(\frac{d}{2}\right)^2 g/v,$$

where d is the bubble diameter, g is gravitational acceleration and v is the kinematic viscosity of water. Using this expression, a gas bubble having a diameter of 0.75 cm will ascend at a rate of about 1.1 ms. Such a bubble will pass through a 1.5 meter deep tank in only 1.4 seconds.

The vertically-oriented gasser tube in the present invention produces a very different result. Liquid pump 70 is configured to produce a flow rate of about 3.5 cubic meters per hour. The gasser tube has in internal diameter of 10 cm in this example, producing a cross sectional area of 0.00785 square meters. Pumping 3.5 cubic meters per hour into this tube produces a modest linear flow rate of only 0.124 m/s.

An exemplary embodiment uses a gasser tube that is 16 meters high. This fact means that it takes 129 seconds (over two minutes) for the liquid flowing at 0.124 m/s to flow from the bottom of the gasser tube to the top.

Of course, gas is also being injected into the gasser tube. Returning to FIG. 5, the reader will recall that gas injector pump 76 injects a gas near the bottom of the gasser tube. In this example, the gas is air. The gas is injected at the rate of 2 cubic feet per minute (0.057 cubic meters per minute or about 3.5 cubic meters per hour). Thus, the liquid and gas injection rates into the bottom of the gasser tube are about equal. The total flow in the injector tube is around 7 cubic meters per hour (gas and liquid combined) so the actual average velocity within the gasser tube is about 0.25 m/s. Even so, the "dwell" of the liquid/gas mixture within the 16 m high tube is still 16/0.25=64 seconds.

Further, the 1-minute-plus dwell is further enhanced by a substantially reduced gas bubble size. The injection mesh shown in FIG. 7 limits the bubble size of the injected gas to between 0.5 mm and 1.0 mm. Those skilled in the art will know that the size of opening in the injecting device (and the pressure across the injection orifice) greatly influence the size of bubble produce. The diameter of a bubble produced is larger than the diameter of the orifice producing it, largely due to surface tension causing the bubble to expand while still attached until its buoyancy causes it to break away and rise through the liquid medium.

Those skilled in the art will also know that the orientation of the injecting device is also influential. Various orientations may be used, but the preferred embodiments in the present invention employ a substantially horizontal plane for mesh 86 (the word "substantially" meaning within 30 degrees of horizontal).

The use of the term "mesh" should not be viewed as limiting. The air injector may assume a wide variety of forms. Injection through a mesh is one form. If a mesh is used then each mesh opening is preferably in the range of 0.15 mm square up to 0.5 mm square. Another option is to use a membrane with a large number of "pore" openings. The openings used in this approach are preferably round holes having a diameter in the range of 0.15 mm to 0.5 mm.

A differential pressure between the injected gas and the liquid in the gasser tube of 1 to 4 bar is used. Assuming an average bubble size of 0.75 mm, the bubble ascent rate can be approximated as:

$$v = \frac{1}{3}\left(\frac{d}{2}\right)^2 g/v$$

Using this expression, a gas bubble having a diameter of 0.75 mm will ascend at the rate of only 0.033 m/s. This ascent rate will be added to the ascent rate of the mixture as a whole. Very roughly speaking, the gas bubbles within the mixture within the gasser tube will ascend at about 0.28 m/s, whereas the liquid will ascend at about 0.22 m/s. This is enough velocity difference to create turbulent mixing and enhance the solution of the gas into the liquid.

The small bubble size produces a much larger surface-area-to-mass ratio for the gas contained in each bubble. Any volume of gas within the gasser tube is very near a liquid-to-gas interface surface at all times. The gas is subjected to this state for about one full minute. By the time the gas has reached the top of the gasser tube, the liquid is preferably saturated. Some excess gas may remain and this simply bubbles out of the reservoir. The reader will recall that—in this example —, the gas is simply ambient air. The escape of some of this air is therefore not a problem.

Prior art systems create a poor scenario for dissolving the gas into the liquid. Most of the gas winds up being segregated into a large gas volume. Further, the "dwell" time of the gas bubbles in the liquid may be only 1 to 2 seconds. For these reasons, the prior art systems have been forced to use concentrated carbon dioxide as the teed gas for a photo-bioreactor.

In contrast, the approach taken in the present invention prevents the formation of large segregated gas volumes, maximizes the surface-area-to-volume ratio for the bubbles, and provides a "bubble-through" time of 1 minute or even more. With these advantages, the present invention is able to use ambient air as the feed gas. To be sure, the present invention could also use concentrated carbon dioxide. However, its ability to feed the photo-bioreactor using air taken from the surrounding atmosphere is significant.

In the prior example the injected gas and the liquid nutrient medium were both flowing in the same direction (upward within the gasser tube). In other embodiments it may be desirable to use a "counterflow" approach in which the gas bubbles rise but the liquid is pumped in a downward direction in the tube. This configuration increases mixing somewhat. More significant, however, is the fact that the downward flow of the liquid may be closely matched to the upward rise rate of the bubbles in order to retain the bubbles in the gasser tube for a longer period of time.

Bubble rise rates do not tend to remain constant over a long period of time, because bubbles eventually aggregate into larger and larger bubbles with a resultant increase in rise rate (larger bubbles rise faster). Thus, one cannot match the downward liquid flow rate with the upward bubble flow rate in order to suspend the bubbles "forever." Some practical ranges may be used however. With a gasifier having a height of 10 m or greater, a downward liquid flow rate of 0.1 to 0.5 m/s works well. A bubble rise rate of 0.1 m/s to 0.3 m/s also works well. These combinations produce a "dwell" time of the gas bubbles in the liquid nutrient medium of 30 seconds or more, with dwell times in excess of one minute being preferable. The dwell time is obviously dependent upon the height of the gasser tube. It is preferable to produce a dwell time of at least 20 seconds. At a 0.5 m/s liquid flow rate, a 10 m high gasser tube would be needed.

Some additional details of the various possible embodiments are listed in the following:

1. The reservoir need not be very large. It can be practically any size and shape. There are operational advantages to mounting it on the top of the photo-bioreactor but it may be located in other places;

2. The gasser tube does not have to be round and it does not have to have a constant cross-section;

3. The bubble-size limiter used in the air injection may be a plate with many holes rather than a wire mesh;

4. The photo-bioreactor can be located near a source of carbon-dioxide pollution, such as a coal-fired power plant. However, it can be located anywhere there is available space and sunlight;

5. It is preferable to match the ascent rate of the liquid nutrient medium and the gas bubbles in the gasser tube so that they are approximately equal, meaning that they are within 0.12 meters per second and even more preferably within 0.08 m/s; and 6. It is preferable to match the volume of liquid nutrient medium and injected gas within the gasser tube so that the volume of one is within 50% of the volume of the other.

Example of Operation

The photo-bioreactor illustrated and described may be operated in a variety of ways to accomplish differing results. The following descriptions should not be viewed as limiting in any way. The use of the photo-bioreactor for the production of biodiesel has been described previously. This process generally involves the promotion of green algae growth to a stable level, followed by filtering and drying. The dried biomass may then be pressed and processed to produce biodiesel and other products in ways known to those skilled in the art.

The photo-bioreactor may also be used for the production of hydrogen. Hydrogen is a natural—albeit transient—product of several microbial driven biochemical reactions. The hydrogen is produced mainly in anaerobic fermentation processes. In addition, certain microorganisms produce enzymes that can catalyze hydrogen synthesis if an outside energy source, like sunlight, is available. The known bio-hydrogen production processes are: (1) Biophotolysis of water using green algae and blue algae (cyanobacteria), through a direct or indirect process; (2) Photofermentation; (3) Dark fermentation; and (4) Hybrid systems combining one or more of these processes.

In this context microalgae could provide several types of different biofuels, including: (1) Microalgae-derived biodiesel; (2) Methane produced through anaerobic digestion of microalgae biomass after lipid extraction; (3) Hydrogen produced by water photolysis during photosynthesis; and (4) Ethanol produced from microalgae biomass after lipid extraction (which is still expected to contain a large carbohydrate mass fraction for fermentation).

Direct biophotolysis is the dissociation of the water molecule due to the action of light energy. This process occurs naturally during green algae photosynthesis. However, the concurrent production of oxygen strongly inhibits the enzyme hydrogenase that catalyzes the production of hydrogen. Therefore, anaerobic conditions are essential for hydrogen production in larger quantities. For large-scale production, the so-called indirect biophotolysis processes have been proposed, in which carbon dioxide is first fixed into carbohydrates and then used in a separate step to produce hydrogen.

Both direct biophotolysis and indirect biophotolysis with filamentous heterocystous cyanobacteria show simultaneous production of oxygen and hydrogen. Either approach would require expensive gas separation. On the other hand, reversible hydrogenase-based indirect biophotolysis processes have, at least conceptually, major advantages over the nitrogenase-based systems. The specific hydrogen evolution activities of reversible hydrogenases are almost a thousand-fold higher than those of nitrogenase and, most importantly, require no expensive adenosine tri-phosphates. Thus, this approach appears to have real practical potential.

Hydrogen production by biophotolysis could be defined as the dissociation of the water molecule through the action of light energy. In the process, sulfur is a key component of the amino acids for the proteins where oxygen is produced during the photosynthesis. Therefore, if one wants to inhibit oxygen production then sulfur nutrient-deprived green algae cultures have good potential for hydrogen production in anaerobic conditions. This is true since the enzyme Fe-hydrogenase, which is responsible for the hydrogen production process using two electrons brought by the protein ferredoxin

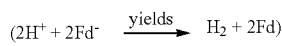

has its activity inhibited by oxygen. However, photosynthesis should not be inhibited in the first stage of the process, so that the desired microalgae can grow and produce biomass.

Hence, the indirect biophotolysis process in a bioreactor should be divided into two separate stages. In the first stage, aerobic conditions (air injection) are applied to increase the biomass up to stabilization. In the second stage, the air supply is cut off and the process continues under anaerobic conditions. In order to use a photo-bioreactor such as shown at FIGS. 5 and 6 for this two-stage process, a cycling regime should be established—as will be explained.

The following reaction summarizes the aerobic first stage of the indirect biophotolysis process:

The following reaction summarizes the anaerobic second stage of the indirect biophotolysis process:

Under this approach, the photo-bioreactor such as shown in FIG. 5 will not be operated in a steady state. Rather, it will first be operated in an aerobic stage to grow the biomass in the presence of air-injection and with oxygen as a significant, circulating product. In the second stage the air supply will be cut off and free hydrogen will be produced.

Even within the stages the reaction rates will vary according to sunlight and temperature. Sunlight only falls on the photo-bioreactor during daylight hours. Even during daylight hours the reaction rates vary with ambient temperature.

The aerobic stage of the process typically runs for about 8 days, at which point the increase rate for the biomass has tapered off. The oxygen concentration is also stable at this point. When the system is switched to the anaerobic stage, the air supply is cut off and the algae perform only mitochondrial respiration. From this point forward the biomass is consumed and its mass fraction decreases. Likewise, the mass fraction of the oxygen decreases during the anaerobic stage since it is consumed by mitochondrial respiration.

In the aerobic stage the carbon dioxide mass fraction remains fairly constant and fairly low (since the carbon dioxide being injected is consumed by the photosynthesis process). In the anaerobic stage the air supply is cut off and the carbon dioxide mass fraction increases.

Hydrogen production is inhibited during the aerobic stage by the absorbed oxygen in the medium, which inhibits the hydrogenase enzyme activity. In fact, the hydrogen mass fraction is practically zero.

However, in the anaerobic stage, as the oxygen starts to be consumed by the microalgae mitochondrial respiration the hydrogen mass fraction will rise. The hydrogenase enzyme starts to catalyze the reaction shown previously. However, hydrogen will only be produced in the presence of carbohydrates ($C_6H_{12}O_6$). Essentially, the carbon dioxide in the injected air is first "fixed" into carbohydrates and then used in the second stage to produce hydrogen. The hydrogen produced bubbles out of the circulating liquid as a gas. It may then be collected, separated, and stored.

The reader will thus appreciate that the present invention provides a comprehensive and space-efficient system for producing biodiesel, hydrogen, or potentially other bio-fuels from microalgae. The foregoing description and drawings comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention.

Many modifications and other embodiments of the invention will come to mind to one skilled in the art to which this invention pertains having the benefit of the teachings presented in the foregoing descriptions and the associated drawings.

Having described our invention, we claim:

1. A method for growing biomass within a liquid nutrient medium, comprising:
   a. providing a support frame, having a top and a bottom;
   b. providing a plurality of separate flow paths supported by said support frame, each of said separate flow paths including a plurality of connected transparent tubes;
   c. providing an inlet manifold connected to an upper end of each of said separate flow paths;
   d. providing an outlet manifold connected to a lower end of each of said separate flow paths;
   e. providing a liquid pump, having an intake side and a discharge side, said intake side being connected to said outlet manifold, said liquid pump being located proximate said bottom of said support frame;

f. providing a gasser tube connected to said discharge side of said liquid pump, said gasser tube being vertically oriented and having a lower portion and an upper portion;
g. said upper portion of said gasser tube being connected to a reservoir, with said reservoir being connected to said inlet manifold;
h. providing a gas injector configured to inject a gas into said lower portion of said gasser tube, thereby creating a mixture of said liquid nutrient medium and said gas in said gasser tube;
i. said gas injector including a bubble size limiter configured to limit an average size of a gas bubble introduced by said gas injector into said liquid nutrient medium to between 0.5 millimeters and 1.0 millimeters;
j. operating said liquid pump at a rate and said gas injector at a rate so that a linear ascent rate of said liquid within said gasser tube is within 0.12 meters pr second of a as bubble ascent rate in said gasser tube; and
k. said gasser tube being at least 10 meters tall.

2. A method for growing biomass as recited in claim 1, wherein said gas is air.

3. A method for growing biomass as recited in claim 2, further comprising:
a. providing an air pump configured to feed pressurized air to said gas injector; and
b. wherein said air pump pulls in ambient air.

4. A method for growing biomass as recited in claim 2, wherein said bubble size limiter is a membrane having pore openings with a diameter between about 0.15 millimeter and 0.5 millimeter.

5. A method for growing biomass as recited in claim 1 wherein said bubble size limiter is a wire mesh having a mesh size 0.15 millimeters square to 0.5 millimeters square.

6. A method for growing biomass within a liquid nutrient medium as recited in claim 1, wherein said gasser tube has a height greater than 10 meters.

7. A method for growing biomass within a liquid nutrient medium as recited in claim 1, wherein said liquid nutrient medium is pumped upward in said gasser tube.

* * * * *